United States Patent [19]

Bauerfeind

[11] Patent Number: 5,181,906
[45] Date of Patent: Jan. 26, 1993

[54] SHOULDER-JOINT BANDAGE

[75] Inventor: Hans B. Bauerfeind, Kempen, Fed. Rep. of Germany

[73] Assignee: Bauerfeind GmbH & Co., Kempen, Fed. Rep. of Germany

[21] Appl. No.: 733,711

[22] Filed: Jul. 22, 1991

[30] Foreign Application Priority Data

Jul. 20, 1990 [DE] Fed. Rep. of Germany ... 9010801[U]

[51] Int. Cl.$^5$ ...................... A61F 13/00; A61F 15/00
[52] U.S. Cl. ........................................ 602/63; 602/61; 602/62; 2/45; 2/310
[58] Field of Search ...................... 602/61, 62, 63, 65, 602/79, 4; 2/45, 310

[56] References Cited

U.S. PATENT DOCUMENTS

| | | | |
|---|---|---|---|
| 380,265 | 3/1888 | Lubin | 2/45 |
| 3,338,236 | 8/1967 | Mcleod, Jr. | 602/19 |
| 4,296,744 | 10/1981 | Palumbo | 602/63 |
| 4,644,946 | 2/1987 | Cremono-Bonato | 602/61 |
| 4,784,128 | 11/1988 | Scheuermann | 602/61 |

Primary Examiner—Paul Prebilic
Attorney, Agent, or Firm—Herbert Dubno

[57] ABSTRACT

A shoulder-joint bandage having an elastic sleeve receiving the upper arm of the patient and a cap passing over the shoulder, has extension belts wound in opposite helical senses along the sleeve and cap and forming a crossover point at the apex of the cap from which the belts extend diagonally downwardly across the back and chest of the patient to a lower crossover point below the armpit of the opposite arm at which the belts are stitched together and have frontal and dorsal connecting segments passing around the back and chest of the patient to be joined by a connecting element at their ends.

13 Claims, 2 Drawing Sheets

SHOULDER-JOINT BANDAGE

FIELD OF THE INVENTION

My present invention relates to a shoulder-joint bandage and, more particularly, to a shoulder-joint bandage of the type in which a sleeve of elastic material receives the upper arm of the patient and has attached thereto a cap of elastic material which covers the shoulder region and the sleeve and cap are affixed to the upper part of the body of the patient by straps.

BACKGROUND OF THE INVENTION

A shoulder-joint bandage is described in EP 02 75 459 as well as commonly owned U.S. Pat. No. 4,784,128. A bandage of this type serves to provide support for the shoulder joint or the acromial clavicular joint in cases of surgical intervention. It is useful in the case of rotator cup rupture, painful shoulder stiffness, subcapital fractures of the humorous, shoulder luxation or shoulder-joint separation to reduce pain and promote the healing process.

While the aforementioned prior art shoulder-joint bandage has been found to be highly satisfactory, it has been found that the comfort of the bandage is sometimes a problem because of a tendency in some cases toward irritation of the armpit region.

OBJECTS OF THE INVENTION

It is, therefore, the principal object of the present invention to provide an improved shoulder-joint bandage whereby the drawback mentioned previously of the prior art shoulder-joint bandage described can be obviated.

Another object of this invention is to provide a shoulder-joint bandage with improved comfort and all of the advantages of the prior art system.

Still another object of my invention is to provide a shoulder-joint bandage which is free from disadvantages of the earlier system and yet is highly satisfactory for the treatment of a variety of shoulder-joint disorders, for promoting healing and for use following surgery to stabilize the shoulder joint.

SUMMARY OF THE INVENTION

These objects and others which will become more readily apparent hereinafter are attained, in accordance with the present invention, in a shoulder-joint bandage which comprises a sleeve of elastic material which fits over the upper arm of the patient and has, extending therefrom, an elastic cap which fits over the shoulder of the patient Extension straps or belts extend from the lower edge of the sleeve helically around the latter in opposite directions and along the edges of the cap to cross over at the apex thereof and then extend, according to the invention, diagonally across the chest and back of the patient to another crossover point at the side of the patient well below the armpit of the opposite arm from which crossover point, in turn, extension straps or belts extend across the back and the chest of the patient substantially horizontally, to be joined together by a connector which may be a pair of VELCRO ® straps, a buckle or the like.

More specifically, therefore, the shoulder-joint bandage of the invention can comprise:

a flexible upper arm sleeve of elastic material adapted to fit over the upper arm of a patient;

a shoulder covering cap of elastic material affixed to the sleeve and having frontal and posterior side edges adjoining at an upper edge of the cap, the sleeve having a lower edge remote from the cap;

a first strap extending from an outermost location at the lower edge along and affixed to the sleeve in a helical turn passing frontally around a underside of the sleeve and then along the posterior edge of the cap to a cross-over point at an apex of the cap, and thereafter extending diagonally downwardly from the apex across a chest of a patient to a lower cross-over point;

a second strap affixed to the sleeve and extending from the location helically in a turn along a posterior of the sleeve around the underside thereof and then along the frontal edge of the cap to the cross-over point at the apex and thereafter diagonally downwardly along the back of the patient to the lower cross-over point; and stitching at the cross-over points for stitching the belts together, each of the belts having attached thereto a respective connecting segment extending from the lower cross-over point around the torso of the patient so that one of the connecting segments extends over the back of the patient and the other of the connecting segments extends across the chest of the patient.

Since the extension belts from the upper crossover point at the apex of the cap extend diagonally downwardly to the opposite side of the torso well below the armpit of the upper arm and are there connected at the lower crossover point and connecting strap segments provided with them run horizontally across the back and the chest, crossover points in the region of an armpit are eliminated. The connecting segments can serve to draw the extension belts firmly against the body and there is, therefore, no concentration of force at the armpit or the region of the armpit to cause possible irritation.

At least the material of the tubular member, i.e. the sleeve, is longitudinally elastic. The two connecting segments can be joined by any connecting means, enabling longitudinal relative mobility of the ends of these strap segments to compensate for various chest expansions and sizes.

According to a feature of the invention, the sleeve and/or the cap-forming section of the bandage can be provided with pockets through which the extension belts can pass.

It is also possible, in accordance with the invention, to provide the cap in the region of the shoulder joint or in the region of the acromion process or the acromio clavicular joint with a pocket for receiving a silicone pad for applying pressure on this region.

BRIEF DESCRIPTION OF THE DRAWING

The above objects, features and advantages of my invention will become more readily apparent from the following description, reference being made to the accompanying drawing in which.

SPECIFIC DESCRIPTION

Figure 1:
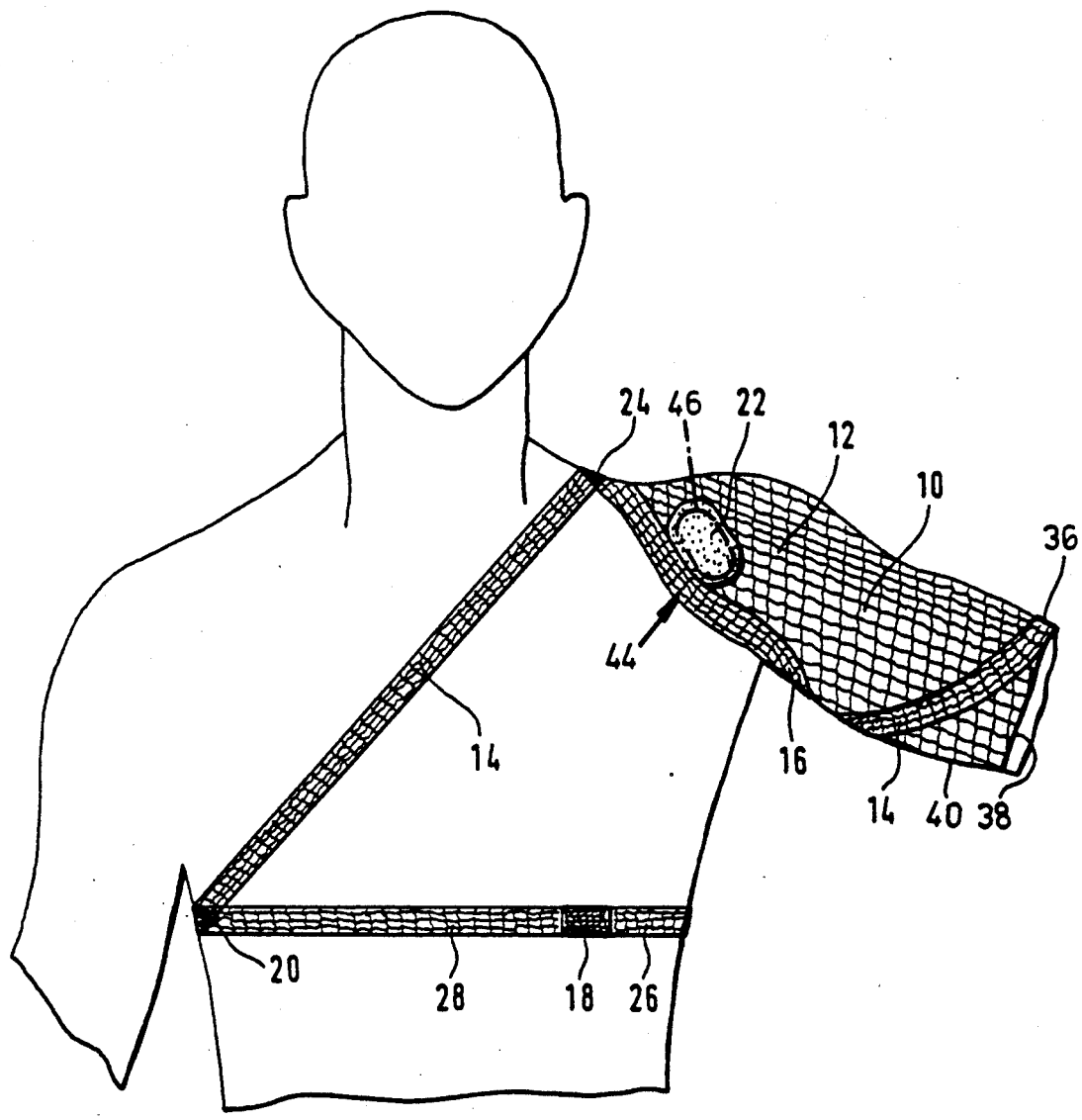
FIG. 1 is a frontal view of the shoulder-joint bandage of the invention.
Figure 3:
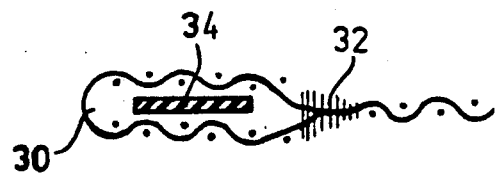
FIG. 3 is a detail showing a pocket in the cap or sleeve receiving the strap.

The shoulder-joint bandage of the present invention comprises a tubular segment 10 engaged around the upper arm of the patient and referred to herein as the upper arm sleeve. This upper arm sleeve is preferably comprised of an elastic material and, most advantageously, is a one-piece tubular knit which can have longitudinal elasticity. At its upper end, the sleeve 10 has a cap-shaped segment or cap 12 of an elastic material which can be knitted unitarily with the sleeve 10 and also may have longitudinal elasticity. Two extension belts 14 and 16 may also be composed of elastic material.

Where the belts 14 and 16 pass along the sleeve and the cap, they can be received in pockets 30 which can be formed by stitching over at 32 a portion of the fabric of the sleeve or cap. The belt within the pocket is represented at 34 in FIG. 3. The first extension belt 14 extends from an upper region 36 of the lower edge 38 of the sleeve 10, at which it may be unitary with a belt 16 or stitched thereto, frontally in a helical pattern along the sleeve 10 to which it is also connected, e.g. in a pocket or by elastic stitching, around the underside 40 of the sleeve 10 (FIG. 1) to then extend upwardly along the posterior edge 42 of the cap 12 to an upper cross-over point 24 at which this strap is stitched to the strap 16 to be discussed in greater detail below.

In rising along the posterior lateral edge 40, the strap or belt 14 passes upwardly from the armpit region of the bandaged shoulder, at an inclination inwardly and upwardly.

From the upper crossover point 24, the belt or strap 14 passes downwardly diagonally across the chest of the patient to a lower crossover point 20 where it is once again stitched to the strap or belt 16. The crossover point 20 is located well below the armpit of the opposite arm across the torso of the patient from the bandaged arm.

Figure 2:
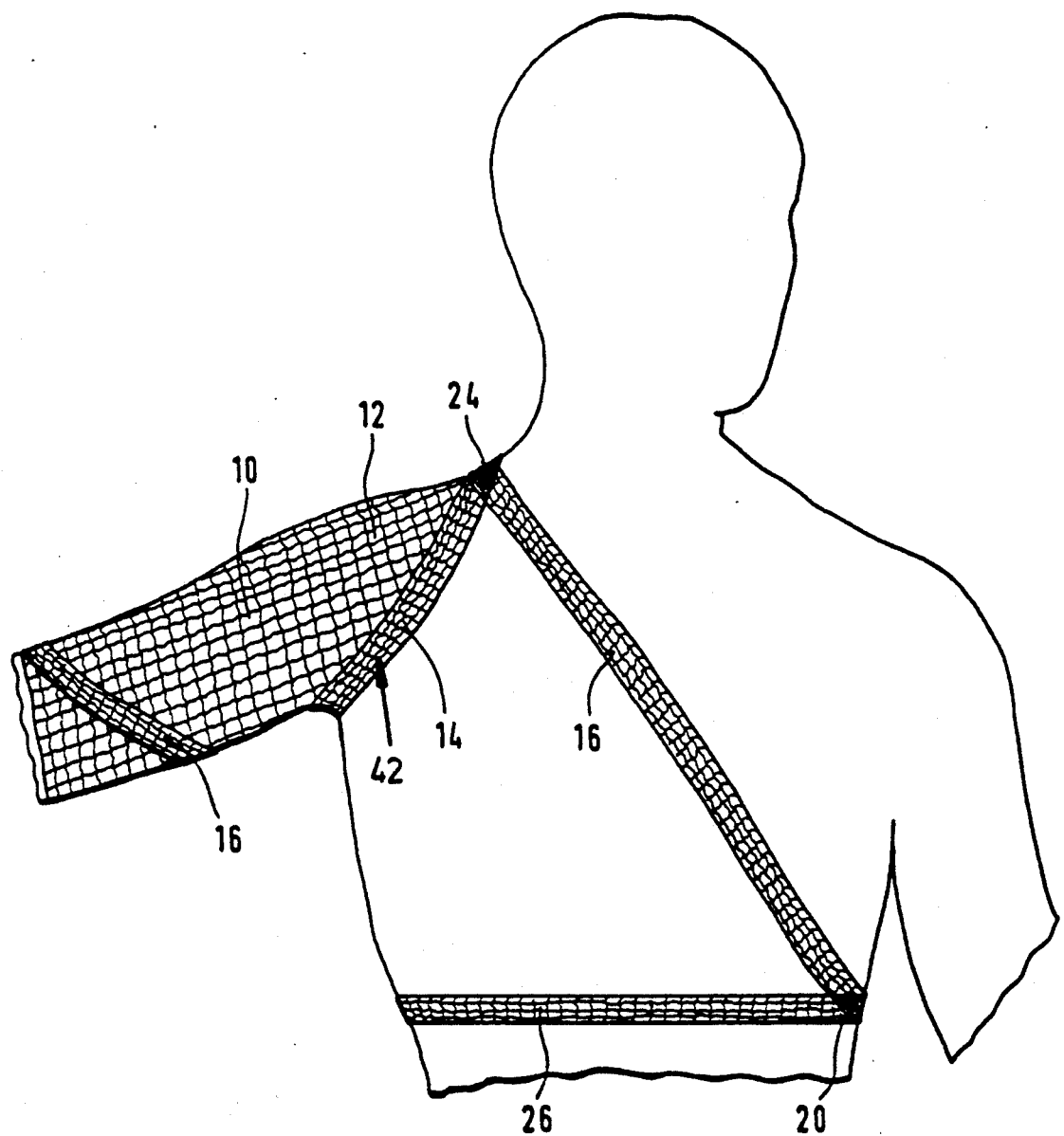
FIG. 2 is a dorsal view of the shoulder-joint bandage.

The second extension belt 16 runs from the region 12 generally helically (FIG. 2) along the posterior side of the sleeve 10 downwardly around the underside of the sleeve 10 and up along the frontal edge 44 of the cap 12 to the crossover point 24 where it passes distally and is stitched to the strap 14. From this upper crossover point 24 the belt 16 is inclined diagonally downwardly across the back of the patient to the lower crossover point 20 where it is stitched to the belt 14 as has already been noted.

A connecting belt segment 26 extends from the first extension belt 14 in the region 20 across the back of the torso substantially horizontally. This extension belt 16 has, in the region of the lower crossover point, a connecting segment 28 extending therefrom and reaching around the chest of the patient, also horizontally.

At their ends, the belt segments 26 and 28 can be connected by an adjustable and releasable connecting member 18 which can be a VELCRO® arrangement as described or a buckle system as mentioned in U.S. Pat. No. 4,784,128.

Like the extension belts 14 and 16, the connecting system 26 and 28 may be elastically extensible. The belts are stitched together at their crossover points 20 and 24.

A pocket 22 can be sewed into the cap 12 in the region of the shoulder-joint to receive a silicone pad 46 (see U.S. Pat. No. 4,784,128) to apply pressure to the shoulder joint as may be desirable for promoting the healing process or stabilizing that joint.

The shoulder-joint bandage of the present invention enables rapid and simple bandaging of the shoulder. The outer rotational effect of the first belt 14 is taken up by the internal rotational effect of the oppositely wound belt 16. Voluntary external and internal rotation, abduction and elevation are all promoted by the belts 14, 16. The portion of the belt extending along the frontal edge of the cap, serves to support the subacromial auxiliary joint.

I claim:
1. A shoulder joint bandage comprising:
   a flexible upper arm sleeve of elastic material adapted to fit over the upper arm of a patient;
   a shoulder covering cap of elastic material affixed to said sleeve and having frontal and posterior side edges adjoining at an upper edge of said cap, said sleeve having a lower edge remote from said cap;
   a first strap extending from an outermost location at said lower edge along and affixed to said sleeve in a helical turn passing frontally around an underside of said sleeve and then along said posterior edge of said cap to a cross-over point at an apex of said cap, and thereafter extending diagonally downwardly from said apex across a chest of a patient to a lower cross-over point;
   a second strap affixed to said sleeve and extending from said location helically in a turn along a posterior of said sleeve around the underside thereof and then along said frontal edge of said cap to said cross-over point at said apex and thereafter diagonally downwardly along the back of said patient to said lower cross-over point; and
   stitching at said cross-over points for stitching said straps together, each of said straps having attached thereto a respective connecting segment extending from said lower cross-over point around the torso of the patient so that one of said connecting segments extends over the back of the patient and the other of said connecting segments extends across the chest of the patient.

2. The shoulder joint bandage defined in claim 1 wherein at least the material of said sleeve is longitudinally elastic.

3. The shoulder joint bandage defined in claim 1, further comprising connecting means for releasably connecting said segments together.

4. The shoulder joint bandage defined in claim 1 wherein said sleeve is formed with pockets in which said straps are received.

5. The shoulder joint bandage defined in claim 1 wherein said cap is formed with pockets in which said straps are received.

6. The shoulder joint bandage defined in claim 1 wherein each of said straps is elastic.

7. The shoulder joint bandage defined in claim 1, further comprising a pressure pad and means forming a pocket for receiving said pressure pad.

8. The shoulder joint bandage defined in claim 7 wherein said pressure pad is provided in a region of an acromion process of a patient and said pressure pad comprises a silicone pad applying pressure on said region.

9. The shoulder joint bandage defined in claim 8 wherein at least the material of said sleeve is longitudinally elastic.

10. The shoulder joint bandage defined in claim 9, further comprising connecting means for releasably connecting said segments together.

11. The shoulder joint bandage defined in claim 10 wherein said sleeve is formed with pockets in which said straps are received.

12. The shoulder joint bandage defined in claim 11 wherein said cap is formed with pockets in which said straps are received.

13. The shoulder joint bandage defined in claim 12 wherein each of said straps is elastic.

* * * * *